# United States Patent [19]

Gras et al.

[11] Patent Number: 5,149,805
[45] Date of Patent: Sep. 22, 1992

[54] PROCESS FOR THE PRODUCTION OF MONOBLOCKED DIISOCYANATES

[75] Inventors: Rainer Gras, Bochum; Elmar Wolf, Recklinghausen; Josef Disteldorf, Marl; Werner Huebel, Recklinghausen; Horst Schnurbusch, Herne, all of Fed. Rep. of Germany

[73] Assignee: Huels Aktiengesellschaft, Marl, Fed. Rep. of Germany

[21] Appl. No.: 243,605

[22] Filed: Sep. 13, 1988

[30] Foreign Application Priority Data

Nov. 21, 1987 [DE] Fed. Rep. of Germany ....... 3739477

[51] Int. Cl.$^5$ .................. C07D 223/10; C07D 223/12; C07C 249/00; C07C 251/00
[52] U.S. Cl. .................... 540/485; 560/330; 560/336; 560/355; 540/527; 540/531
[58] Field of Search ....................... 560/330, 336, 355; 540/527, 531, 485

[56] References Cited

U.S. PATENT DOCUMENTS

| 2,723,265 | 11/1955 | Stallmann | 560/330 |
| 3,723,372 | 3/1973 | Wakimoto et al. | 560/330 |
| 3,926,875 | 12/1975 | Tsugukuni et al. | 560/330 |
| 4,292,350 | 9/1981 | Kubitza et al. | 560/330 |
| 4,920,173 | 4/1990 | Gras | 560/330 |

FOREIGN PATENT DOCUMENTS

| 2020905 | 4/1970 | Fed. Rep. of Germany | 560/330 |
| 1043008 | 11/1953 | France | 560/330 |
| 1233866 | 10/1960 | France | 560/330 |
| 1378974 | 1/1975 | United Kingdom | 560/330 |

Primary Examiner—Mary C. Lee
Assistant Examiner—Robert C. Whittenbaugh
Attorney, Agent, or Firm—Oblon, Spivak, McClelland, Maier & Neustadt

[57] ABSTRACT

Monoblocked diisocyanates which contain little free and diblocked diisocyanate are obtained by a process which involves adding 1 mole of a blocking agent to a diisocyanate which is present in excess and subsequently removing the excess diisocyanate by thin film evaporation. The compounds produced are useful for the production of cataphoresis resins.

10 Claims, No Drawings

PROCESS FOR THE PRODUCTION OF MONOBLOCKED DIISOCYANATES

BACKGROUND OF THE INVENTION

1. Field of the Invention

The present invention relates to a process for the production of monoblocked diisocyanates and the products thereof.

2. Discussion of the Background

Complete blocking of isocyanates for temporary protection of their NCO groups has been known for a long time and is carried out on a technical scale, e.g., in the production of 1-K-PUR powder or 1-K fired enamels which contain solvents. A 1-K-PUR powder is a powder containing a blocked isocyanate and a hydroxyl group containing compound. 1-K fired enamels additionally contain a solvent. These mixtures are stable at room temperature. However, when heated the blocking group splits off and a reaction between the isocyanate and the hydroxyl groups occurs.

Monoblocking of diisocyanates, i.e., using one mole of monofunctional blocking agent per mole of diisocyanate, is also known to the art. Monoblocked diisocyanates are useful in the manufacture of polyisocyanate-urea-adducts as disclosed in copending U.S. Pat. application Ser. No. 07/245,217, filed Sep. 16, 1988, which is incorporated herein by reference.

The process for the production of these monoblocked diisocyanates involves the following steps: (i) adding the blocking agent to the diisocyanate, which may be dissolved in an inert solvent, at room temperature up to 120° C., in increments, and (ii) heating this mixture until the calculated NCO content is reached. For example, according to DE-OS 31 43 060, an isophorone diisocyanate monoblocked with epsilon caprolactam is produced by the reaction of 1 mole of isophorone diisocyanate (IPDI, also called 3-isocyanatomethyl-3,5,5-trimethylcyclohexylisocyanate) and 1 mole of epsilon caprolactam at 120° C.

An IPDI monoblocked with epsilon caprolactam produced in this way still contains approximately 16% non-converted IPDI, however This is easily understandable, since with an equimolar mixture of IPDI and epsilon caprolactam, the reaction cannot be controlled in such a way that 1 mole of IPDI always reacts only with 1 mole of epsilon caprolactam. To the extent that diblocked IPDI forms, free IPDI remains, i.e., the reaction product of 1 mole of IPDI and 1 mole of epsilon caprolactam (and this basically applies to all diisocyanates and their conversion with monofunctional blocking agents) is always a mixture of IPDI monoblocked with epsilon caprolactam, IPDI diblocked with epsilon caprolactam, and free IPDI.

Thus, there is a need for a process to produce monoblocked diisocyanates with only a slight formation of free diisocyanate and diblocked diisocyanate.

There is a further need for a process for the production of monoblocked cycloaliphatic diisocyanates with only slight formation of free diisocyanate and diblocked diisocyanate.

SUMMARY OF THE INVENTION

Accordingly, one object of the present invention is to provide a novel process for the production of monoblocked diisocyanates with only a slight formation of free diisocyanate and diblocked diisocyanate.

A further object of the present invention is to provide a novel process for the production of monoblocked cyclo-aliphatic diisocyanates with only a slight formation of free cycloaliphatic diisocyanate and diblocked cycloaliphatic diisocyanate. The diisocyanate-content is less than 6,5 weight percent, especially less than 1 weight percent.

A still further object of the present invention is to provide a novel process for the production of monoblocked IPDI with only a slight formation of free and diblocked IPDI.

These and other objects have been achieved by the inventors' discovery that monoblocked diisocyanates with a low content of free diisocyanate and diblocked diisocyanate may be formed by a process in which 1 mole of blocking agent is added to a great excess of diisocyanate and then substantially all of the unreacted diisocyanate is removed from the reaction mixture.

DETAILED DESCRIPTION OF THE PREFERRED EMBODIMENTS

The present process is applicable to any diisocyanate which can be distilled at a temperature lower than the deblocking temperature of the monoblocked diisocyanates. The following diisocyanates have proven to be particularly suitable: hexamethylene diisocyanate (HDI), 2-methyl-1,5-diisocyanatopentane (DI51), 2-ethyl-1,4-diisocyanatobutane, 1,5-diisocyanatohexane, 1,10-diisocyanatodecane, 1,9-diisocyanato-5-methylnonane, dodecamethylene diisocyanate, isophorone diisocyanate (IPDI), hexahydroxylylene-1,4-diisocyanate or hexahydroxylylene-1,3-diisocyanate.

The present process may utilize any suitable diisocyanate blocking agent. Preferred blocking agents include, for example, epsilon caprolactam, methylethylketoxime, and diisobutylketoxime.

The mole ratio of diisocyanate to blocking agent depends on the content of diblocked diisocyanate which can be permitted. The higher the excess of diisocyanate, the lower the content of diblocked diisocyanate. Typically, 1 mole of blocking agent is added to from 5 to 20 moles of diisocyanate.

The process of the present invention may be conveniently carried out by heating the reaction mixture to a temperature of up to 120° C. Alternatively, the present process may comprise mixing the blocking agent and diisocyanate at room temperature. The reaction of the blocking agent with the diisocyanate in the present process may be carried out neat, that is without solvent or diluent.

The reaction time of the present invention is determined by the relative reactivities of the blocking agent and the diisocyanate. Thus, the blocking agent and diisocyanate are stirred together until 1 equivalent, based on blocking agent, of NCO groups is consumed.

When the expected NCO content is reached, substantially all of the excess diisocyanate is removed from the reaction product. It is preferred that the excess diisocyanate be removed by thin film evaporation at a reduced pressure of approximately from 0.1 to 0.2 mbar. The distillation temperature is determined by the boiling point of the diisocyanate to be distilled and lies in a range of from 90° to 140° C.; for hexamethylene diisocyanate it is 90° C., for example, and for IPDI 130° C. For separation of the diisocyanate on a technical scale, it has proven to be practical to use two steps, i.e. two thin film evaporators which follow one another, with the main amount (approximately 80%) being removed in the first thin film evaporator, and the remaining amount being separated in the second thin film evaporator.

The present process can be used to produce monoblocked diisocyanates which contain only a slight amount of free and diblocked diisocyanate. Thus, addition of 1 mole of blocking agent to from 5 to 20 moles of diisocyanate followed by thin film evaporation of the excess diisocyanate produces mixtures which contain less than from 6.5% preferably less than 1.0% by weight of free diisocyanate. The content of free NCO groups of the compounds produced according to the invention is, depending on the diisocyanate, from 11 to 18% by weight. The total content of NCO groups is from 23 to 35% by weight.

The viscosity at room temperature of the compounds according to the present invention varies in a wide range, from 100 to $10^6$ mPas. The compounds produced according to the present invention are very well suited for the production of cataphoresis resins.

Other features of the invention will become apparent in the course of the following descriptions of exemplary embodiments which are given for illustration of the invention and are not intended to be limiting thereof.

EXAMPLES 1 TO 9

General Procedure

One mole of blocking agent is added to from 5 to 20 moles of diisocyanate at a temperature of from room temperature up to 120° C., in increments, while stirring intensively. After addition of the blocking agent has been completed, the reaction mixture is heated at 100° C. for approximately 1 hour, and, subsequently, the excess diisocyanate is removed by thin film evaporation at a temperature of from 90° to 140° C. and a pressure of 0.133 mbar. The chemical and physical characteristics determined for the reaction product are summarized in the following table.

(i) reacting a blocking agent with a diisocyanate in a ratio of 1 mole of said blocking agent to 5 to 20 moles of said diisocyanate to obtain a reaction mixture which contains monoblocked diisocyanate and excess diisocyanate; and (ii) removing said excess diisocyanate from said reaction mixture to obtain a composition containing said monoblocked diisocyanate and not more than 6.5 wt.% of free diisocyanate, wherein said diisocyanate is one member selected from the group consisting of hexamethylene diisocyanate, 2-methyl-1,5-diisocyanatopentane, 2-ethyl-1,4-diisocyanatobutane, 1,5-diisocyanatohexane, 1-10-diisocyanatodecane, 1,9-diisocyanato-5-methylnonane, dodecamethylene diisocyanate, isophorone diisocyanate, hexahydroxylylene-1,4-diisocyanate and hexahydroxylylene-1,3-diisocyanate; and said removing step comprises thin film evaporation of said excess diisocyanate.

2. The monoblocked diisocyanate composition of claim 1, wherein said reacting step comprises adding said blocking agent to said diisocyanate in a temperature range of from room temperature to 120° C.

3. The monoblocked diisocyanate composition of claim 1, wherein said thin film evaporation is carried out in a temperature range of from 90° to 140° C.

4. The monoblocked diisocyanate composition of claim 1, wherein said thin film evaporation is carried out at a reduced pressure.

5. The monoblocked diisocyanate composition of claim 4, wherein said reduced pressure comprises a pressure of from 0.1 to 0.2 mbar.

6. The monoblocked diisocyanate composition of claim 1, wherein said diisocyanate is a (cyclo)aliphatic diisocyanate.

7. The monoblocked diisocyanate composition of claim 1, wherein said blocking agent is one member

|  | Starting Materials | | Reaction Products | | | Viscosity | | |
|---|---|---|---|---|---|---|---|---|
| Example | Diisocyanate | Blocking Agent | NCO-free % | NCO total % | Free Diisocyanate % | mPas at 25° C. | mPas at 40° C. | mPas at 50° C. |
| 1 | IPDI | epsilon-caprolactam | 11.8 | 24.6 | 1.0 | $125 \times 10^4$ | $63.5 \times 10^3$ | $13.7 \times 10^3$ |
| 2 | IPDI | epsilon-caprolactam | 11.5 | 24.5 | 2.2 | $114.5 \times 10^4$ | $61.2 \times 10^3$ | $12.5 \times 10^3$ |
| 3 | IPDI | epsilon-caprolactam | 11.6 | 24.5 | 3.5 | $112 \times 10^4$ | $59.5 \times 10^3$ | $11.5 \times 10^3$ |
| 4 | IPDI | epsilon-caprolactam | 11.8 | 24.5 | 4.6 | $66 \times 10^4$ | $34 \times 10^3$ | $8.5 \times 10^3$ |
| 5 | IPDI | MEK-oxime* | 12.8 | 26.5 | 2.8 | $57.1 \times 10^4$ | $27.5 \times 10^3$ | $5.5 \times 10^3$ |
| 6 | HDI | epsilon-caprolactam | 15.3 | 29.4 | 0.5 | 100 | 50 | 30 |
| 7 | HDI | MEK-oxime* | 15.8 | 32.4 | 2.5 | 70 | 50 | 30 |
| 8 | DI51 | epsilon-caprolactam | 14.8 | 29.3 | 0.7 | 160 | 60 | 45 |
| 9 | DI51 | MEK-oxime* | 15.7 | 31.5 | 0.8 | 190 | 80 | 60 |

*MEK-oxime = Methylethylketoxime

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A monoblocked diisocyanate composition produced by a process comprising the steps of:

selected from the group consisting of epsilon caprolactam, methylethylketoxime and diisobutylketoxime.

8. The monoblocked diisocyanate composition of claim 7, wherein said blocking agent is epsilon caprolactam.

9. A monoblocked diisocyanate composition containing not more than 6.5 wt.% of free diisocyanate corresponding to said monoblocked diisocyanate.

10. The monoblocked diisocyanate composition of claim 9, containing not more than 1 wt.% of said free diisocyanate.

* * * * *